(12) United States Patent
Appel et al.

(10) Patent No.: US 11,542,401 B2
(45) Date of Patent: Jan. 3, 2023

(54) WHITISH WRITING AND MARKING FLUID FOR CAPILLARY SYSTEMS AND WRITING INSTRUMENT

(71) Applicant: FABER-CASTELL AG, Stein (DE)

(72) Inventors: Tatiana Appel, Oberasbach (DE); Gerhard Lugert, Nuremberg (DE); Kurt Seidl, Alkoven (AT)

(73) Assignee: Faber-Castell AG, Stein (DE)

( * ) Notice: Subject to any disclaimer, the term of this patent is extended or adjusted under 35 U.S.C. 154(b) by 916 days.

(21) Appl. No.: 16/383,892

(22) Filed: Apr. 15, 2019

(65) Prior Publication Data

US 2019/0315982 A1    Oct. 17, 2019

(30) Foreign Application Priority Data

Apr. 13, 2018 (EP) .................................. 18167327

(51) Int. Cl.
| | |
|---|---|
| *C09D 11/17* | (2014.01) |
| *B43K 8/02* | (2006.01) |
| *C08K 3/22* | (2006.01) |
| *C08K 5/053* | (2006.01) |
| *C08L 75/04* | (2006.01) |
| *C08L 83/12* | (2006.01) |

(52) U.S. Cl.
CPC .............. *C09D 11/17* (2013.01); *B43K 8/026* (2013.01); *C08K 3/22* (2013.01); *C08K 5/053* (2013.01); *C08K 2003/2237* (2013.01); *C08L 75/04* (2013.01); *C08L 83/12* (2013.01)

(58) Field of Classification Search
None
See application file for complete search history.

(56) References Cited

U.S. PATENT DOCUMENTS

| | | | | |
|---|---|---|---|---|
| 2006/0107873 | A1* | 5/2006 | El-Shoubary | C09C 3/006 106/499 |
| 2007/0060670 | A1 | 3/2007 | Ellis | |
| 2012/0316276 | A1 | 12/2012 | Iwasa et al. | |
| 2015/0184010 | A1 | 7/2015 | Okada et al. | |
| 2017/0051169 | A1 | 2/2017 | Kasperchik et al. | |
| 2017/0051170 | A1* | 2/2017 | Nakagawa | B41M 7/009 |
| 2017/0258702 | A1* | 9/2017 | Costanzo | A61K 8/894 |

FOREIGN PATENT DOCUMENTS

| | | | |
|---|---|---|---|
| EP | 2514792 A1 | | 10/2012 |
| EP | 2891691 A1 | | 7/2015 |
| EP | 3 680 298 | * | 7/2020 |
| WO | 2015142335 A1 | | 9/2015 |

* cited by examiner

*Primary Examiner* — Robert T Butcher
(74) *Attorney, Agent, or Firm* — Laurence A. Greenberg; Werner H. Stemer; Ralph E. Locher

(57) ABSTRACT

A whitish writing and/or marking fluid, in particular white writing and/or marking fluid, for writing instruments, in particular for capillary writing instruments, or for cosmetic applications, that has a viscosity of less than 30 mPa s (Brookfield, 20° C., cone plate CPE-40), and contains 5 to 15 wt % of an anionic dispersion of a hard resin, an aqueous titanium dioxide dispersion, and a preservative.

16 Claims, 1 Drawing Sheet

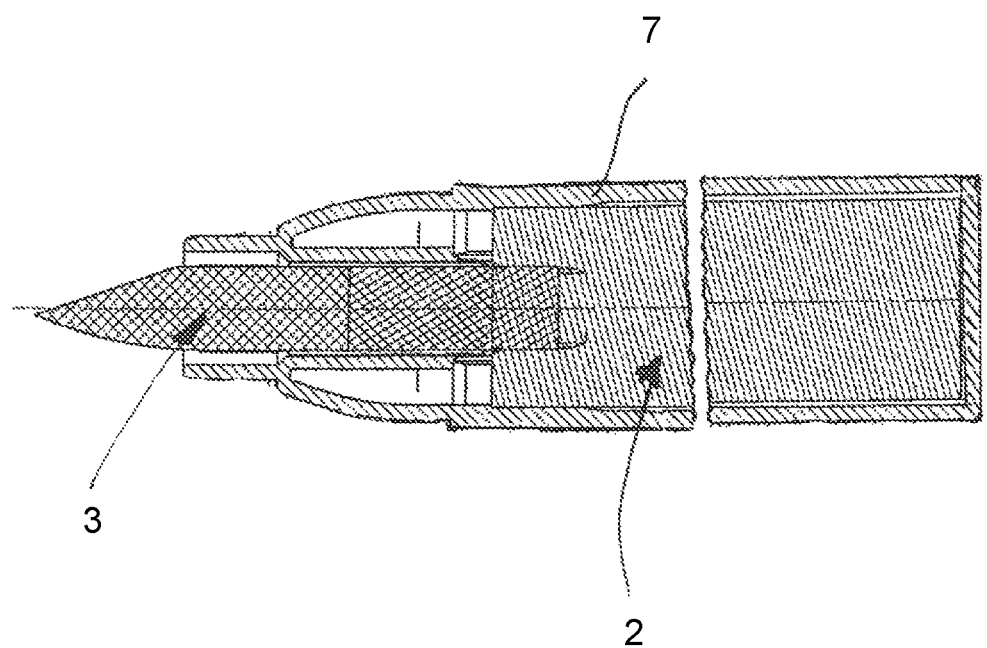

WHITISH WRITING AND MARKING FLUID FOR CAPILLARY SYSTEMS AND WRITING INSTRUMENT

CROSS-REFERENCE TO RELATED APPLICATION

This application claims the priority, under 35 U.S.C. § 119, of European application EP18167327.8, filed Apr. 13, 2018; the prior application is herewith incorporated by reference in its entirety.

BACKGROUND OF THE INVENTION

Field of the Invention

The invention relates to a whitish writing and/or marking fluid, in particular a white writing and/or marking fluid, for writing instruments, in particular for capillary writing instruments, or for cosmetic applications, and to a writing instrument in which such writing and/or marking fluid is used.

Colored marking fluids for markers based on organic solvents, such as alcohols, esters, ketones or aromatic solvents such as toluene or xylene, have long been known in the art. For the colorants, usually pigments, cationic dyes, fat-soluble dyes or metal-complex dyes are used, together with one or more wetting agents and resins. White or light pastel-colored writing and/or marking fluid that has a high degree of whiteness and covering capacity may only be achieved on a pigment base. Examples of white pigments are e.g. kaolin, chalk or titanium dioxide, with titanium dioxide-based writing and marking fluids having a higher covering capacity and a higher degree of whiteness. Known writing and marking fluids with titanium dioxide pigments, however, have a very high density and a strong tendency to sediment. Sedimentation may be counteracted by increasing the viscosity of such a fluid to values significantly greater than 20 cP (Brookfield method, 20° C.). However, to date, highly viscous fluids may only be applied as colors.

Writing instruments in which such writing and/or marking fluids are used comprise a shaft, typically a plastic or metal housing, on which a cap is placed when not in use. A reservoir for the writing and/or marking fluid made of a capillary material, for example polyester or polyolefin fibers, is arranged in the interior of the shaft and is fluidically connected to an applicator element made of a likewise capillary material, for example a fiber or sinter tip, so that the writing and/or marking fluid may be transported from the reservoir to the tip of the applicator element due to adhesive forces or the capillary effect.

In another variant of a writing instrument, a valve system is used, in which the writing and/or marking fluid is filled into a reservoir inside the shaft as a free-flowing fluid and fluid is dispensed via a writing or marking tip that is preferably made of polyester or acrylic fibers or also of sintered polyolefins. A valve is furnished between the tip and the reservoir to ensure a controlled delivery of the fluid.

In this latter system, particularly in the case of highly viscous, pigmented fluids, one or more mixing balls are often used in the fluid, so that the fluid may be homogenized by shaking the writing instrument before applying the fluid. In addition, a pump is also required in order to apply the fluid. Users perceive this necessary shaking and pumping as a drawback. The pump system does not allow using very fine tips or highly precise application behavior.

Such mixing balls cannot be used in capillary systems. To ensure sufficient application, the fluids used in capillary systems must also have very low viscosities of less than 50 mPa s, but preferably less than 20 mPa s (Brookfield, 20° C., cone plate CPE-40).

Industrial markers usually contain more-viscous white or colored writing and/or marking fluids and, due to their high viscosity (greater than 50 mPa s, 20° C. Brookfield, cone plate CPE-40), they cannot be applied via conventional capillary systems, but only via valve systems.

SUMMARY OF THE INVENTION

Accordingly, the objective of this invention is to propose a whitish writing and/or marking fluid, in particular a white writing and/or marking fluid, for a writing instrument, in particular a capillary writing instrument, or cosmetic applications, that is improved with regard to the drawbacks and problems described. A further objective of the invention is to provide a writing instrument, in particular a capillary writing instrument, in which the writing and/or marking fluid is used.

The whitish writing and/or marking fluid according to the invention, in particular white writing and/or marking fluid, for writing instruments, in particular for capillary writing instruments, or cosmetic applications, has a viscosity of less than 30 mPa s (Brookfield, 20° C., cone plate CPE-40). The writing and/or marking fluid contains an aqueous titanium dioxide dispersion, 5 to 15 wt % of a dispersion of a hard resin and a preservative.

"Whitish writing and/or marking fluid" denotes writing and/or marking fluid with a high white content, and in particular one that is white or has a slight pastel tint.

Surprisingly, it has been found that such writing and/or marking fluid is stabilized to such an extent that it may be used over several months and may be used in capillary systems, without forming problematic deposits in the capillary reservoir of the tip. A titanium dioxide dispersion used as pigment preparation according to the invention (titanium dioxide Color Index Pigment White 6 (77891), CAS No. 13463-67-7), also referred to as a titanium white paste, has in particular a solid content of between 70 and 75 wt %, the pigment being rutile, i.e. tetragonal TiO2. The titanium white paste has a density according to ISO 787/10 of 2.2±0.1 $g/cm^3$, a viscosity of 400 mPa s and a pH value between 7.5 and 8.5. The titanium white paste also has a pigment particle size D90 of 0.3 μm when measuring the diameter for example with the wet CILAS 920 method, and an average pigment particle size D50 of 0.25 μm.

The writing and/or marking fluid contains in particular 45 to 70 wt %, preferably 50 to 65 wt %, preferably 55 to 60 wt %, of the titanium white paste.

In a preferred embodiment, the hard resin is a polyurethane polyol resin, and the dispersion of a hard resin is an anionic dispersion of a polyurethane polyol resin.

An anionic dispersion of a polyurethane polyol resin has in particular the following properties:

| | | |
|---|---|---|
| a) | Viscosity at 23° C. (in supplied form) | Approx. 400 mPa s |
| b) | pH (in supplied form) | Approx. 9 |
| c) | Solvent | Water |

Such an anionic dispersion of a polyurethane polyol resin is available, for example, under the trade name TEGO® VariPlus DS 50.[1]

For the preservative, one or more of formaldehyde releasers, phenoxyethanol, parabens and isothiazolinones may expediently be used.

A suitable preservative that provides a formaldehyde releaser is for example available under the trade name ACTICIDE SR 7034[3]. The preservative known in the art is a biocide based on 1,6-dihydroxy-2,5-dioxahexane and tetramethylolacetylenediurea; under environmental conditions, 1,6-dihydroxy-2,5-dioxahexane hydrolyzes into formaldehyde and ethylene glycol.

Another suitable preservative, for example, is available under the trade name ACTICIDE LT2[4]. The preservative is an isothiazolinone-based biocide containing 2-bromo-2-nitropropane-1,3-diol and 2-octyl-2H-isothiazol3-one.

The composition of the writing and/or marking fluid also contains 1.0 to 3.0 wt % of a wetting agent, in particular a silicone wetting agent. Expediently, the silicone wetting agent is a polyethylene-modified polysiloxane. One such polyethylene-modified polysiloxane, for example, is available under the trade name ABIL B 8851[2]. Polyethylene-modified polysiloxane is soluble in water and has a dynamic viscosity of 330 to 570 mPa s at 25° C. as supplied.

The design of the writing and/or marking fluid comprises wetting agents, in particular glycerin and/or glycols or polyalcohols. For example, among glycols, butylene glycol or propylene glycol may be used. Expediently, up to 15 wt % of wetting agents are added, in particular 3 to 10 wt %, in particular 5 to 8 wt %.

In an embodiment, the writing and/or marking fluid contains additional additives selected from among antiblocking additives, in particular a colloidal dispersion of silicon dioxide particles and/or polyether-modified polydimethylsiloxanes. Antiblocking additives according to the invention are for example marketed under the trade names Borchi Coll 10[5], Borchi Coll 20[6], Borchi Coll 20M[7], Borchi Coll 30[8], and a polyether-modified polydimethylsiloxane is marketed as BYK 3455[9].

The antiblocking additives have the following properties:
a) Viscosity at 23° C. (as supplied) 3-7 mPa s, particularly 5 mPa s
b) pH (as supplied) approx. 8.5-10.5, particularly 8.5-9.5.

Expediently, the additional additives are added in a total quantity of up to 10 wt %.

In an embodiment, the design of the writing and/or marking fluid may contain blue dyes or pigments at a concentration of no more than 0.2 wt %. Adding a small amount of blue dye or blue pigments, such as patent blue or ultramarine, increases the brightness of the color.

In an alternative embodiment, the writing and/or marking fluid may contain dyes or pigments in a concentration of no more than 3.0 wt %. In this way, writing and/or marking fluid with a colored tint may be obtained, such as pastel yellow or pastel red.

The writing instrument according to the invention contains a writing tip made of a capillary material and a reservoir that is made of a capillary material and contains a writing and/or marking fluid according to the invention.

Other features which are considered as characteristic for the invention are set forth in the appended claims.

Although the invention is illustrated and described herein as embodied in a whitish writing and marking fluid for capillary systems, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWING

The single FIGURE of the drawing is a diagrammatic, longitudinal sectional view of a capillary writing instrument according to the invention.

DETAILED DESCRIPTION OF THE INVENTION

Referring now to the single FIGURE of the drawing in detail, there is shown a writing instrument, such as a marker, is substantially stylus-shaped and has a shaft 1 in which there is a reservoir 2 is made of a capillary material or a low-density fiber reservoir, such as a polyester fiber reservoir. The front end of the stylus bears a writing tip 3 made of a capillary material, or a fiber tip the rear end of which is connected to or projects into the fiber reservoir 2.

Writing and/or marking fluid is chiefly manufactured in mixing tanks in which the other components, for example colorants or additives, are added to the pigment dispersion. The components are continuously homogenized with a stirrer in order to mix them intensively and distribute them with sufficient evenness. The writing and/or marking fluid thus obtained is then poured into the reservoir 2 of the above-described writing instrument that is made of capillary material.

Seven exemplary formulations for white writing and marking fluids are set forth below. The amounts in the sample formulations are given in wt %.

Example 1

| | |
|---|---|
| Demineralized water | 27.40 |
| Silicone wetting agent | 2.00 |
| Polyether-modified polydimethylsiloxane | |
| Formaldehyde releaser | 0.40 |
| Isothiazolinone-based preservative | 0.20 |
| Glycerin | |
| Propylene glycol | |
| Polyurethane polyol resin | 10.00 |
| Titanium white paste | 60.00 |
| Antiblocking additive | |
| Additional colorant | |
| | 100.00 |

Due to its high titanium white paste content, a writing and/or marking fluid with a composition corresponding to Example 1 has good coverage and good long-term stability.

Example 2

| | |
|---|---|
| Demineralized water | 24.40 |
| Silicone wetting agent | 2.00 |
| Polyether-modified polydimethylsiloxane | |
| Formaldehyde releaser | 0.40 |
| Isothiazolinone-based preservative | 0.20 |
| Glycerin | 5.00 |
| Propylene glycol | |
| Polyurethane polyol resin | 10.00 |

| | |
|---|---|
| Titanium white paste | 58.00 |
| Antiblocking additive | |
| Additional colorant | |
| | 100.00 |

A writing and/or marking fluid with a composition corresponding to Example 2 has a high proportion of wetting agent.

Example 3

| | |
|---|---|
| Demineralized water | 23.40 |
| Silicone wetting agent | 2.00 |
| Polyether-modified polydimethylsiloxane | 1.00 |
| Formaldehyde releaser | 0.40 |
| Isothiazolinone-based preservative | 0.20 |
| Glycerin | 5.00 |
| Propylene glycol | |
| Polyurethane polyol resin | 10.00 |
| Titanium white paste | 58.00 |
| Antiblocking additive | |
| Additional colorant | |
| | 100.00 |

A writing and/or marking fluid having a composition according to Example 3 contains a polyether-modified polydimethylsiloxane, which improves substrate wetting and flow, because the surface tension is reduced. This composition allows use on substrates that are difficult to wet.

Example 4

| | |
|---|---|
| Demineralized water | 21.40 |
| Silicone wetting agent | 2.00 |
| Polyether-modified polydimethylsiloxane | |
| Formaldehyde releaser | 0.40 |
| Isothiazolinone-based preservative | 0.20 |
| Glycerin | |
| Propylene glycol | |
| Polyurethane polyol resin | 10.00 |
| Titanium white paste | 60.00 |
| Antiblocking additive | 6.00 |
| Additional colorant | |
| | 100.00 |

A writing and/or marking fluid that has a composition corresponding to Example 4 contains an antiblocking additive, in particular a non-sedimenting colloidal dispersion of silicon dioxide nanoparticles. This additive influences drying and improves the adhesion of the writing and/or marking fluid to wood, plastic and metal surfaces while also increasing coverage.

Example 5

| | |
|---|---|
| Demineralized water | 28.90 |
| Silicone wetting agent | 1.00 |
| Polyether-modified polydimethylsiloxane | 0.50 |
| Formaldehyde releaser | 0.40 |
| Isothiazolinone-based preservative | 0.20 |
| Glycerin | |
| Propylene glycol | 5.00 |
| Polyurethane polyol resin | 14.00 |
| Titanium white paste | 50.00 |
| Antiblocking additive | |
| Additional colorant | |
| | 100.00 |

A writing and/or marking fluid with a composition corresponding to Example 5 contains propylene glycol as an alternative wetting agent and a comparatively low proportion of titanium white paste.

Example 6

| | |
|---|---|
| Demineralized water | 16.40 |
| Silicone wetting agent | 3.00 |
| Polyether-modified polydimethylsiloxane | |
| Formaldehyde releaser | 0.40 |
| Isothiazolinone-based preservative | 0.20 |
| Glycerin | 7.00 |
| Propylene glycol | |
| Polyurethane polyol resin | 6.00 |
| Titanium white paste | 65.00 |
| Antiblocking additive | 2.00 |
| Additional colorant | |
| | 100.00 |

A writing and/or marking fluid with a composition corresponding to Example 6 has a high proportion of titanium white paste.

Example 7

| | |
|---|---|
| Demineralized water | 27.20 |
| Silicone wetting agent | 2.00 |
| Polyether-modified polydimethylsiloxane | |
| Formaldehyde releaser | 0.40 |
| Isothiazolinone | 0.20 |
| Glycerin | |
| Propylene glycol | |
| Polyurethane polyol resin | 10.00 |
| Titanium white paste | 60.00 |
| Antiblocking additive | |
| Additional colorant | 0.20 |
| | 100.00 |

A writing and/or marking fluid with a composition corresponding to Example 7 has an additional colorant, in this case 0.2 wt % of ultramarine blue. The additional colorant produces a slightly bluish white, which leads to increased brightness.

Product designations/manufacturers:

1) Evonik Resource Efficiency GmbH, 45127 Essen, Germany

2) Evonik Industries AG, 45127 Essen, Germany

3), 4) THOR GmbH, 67346 Speyer, Germany

5), 6), 7), 8) OMG Borchers GmbH, 40764 Langenfeld, Germany

9) BYK-Chemie GmbH, 46462 Wesel, Germany

The invention claimed is:

1. A whitish writing and/or marking fluid for writing instruments or for cosmetic applications, the whitish writing and/or marking fluid comprising:
   a viscosity of less than 30 mPa s;
   an aqueous dispersion of titanium dioxide in an amount of 45 to 70 wt % of a total weight of the whitish writing and/or marking fluid, a solid content of said aqueous dispersion of titanium dioxide being 70 to 75 wt % of said aqueous dispersion;
   an anionic dispersion of a hard resin in an amount of 5 to 15 wt % of the total weight of the whitish writing and/or marking fluid;
   a silicone wetting agent in an amount of 1.0 to 3.0 wt % of the total weight of the whitish writing and/or marking fluid;
   a preservative; and
   a remainder of water.

2. The writing and/or marking fluid according to claim 1, wherein said aqueous dispersion of titanium dioxide is 50 to 65 wt % of the total weight of the whitish writing and/or marking fluid.

3. The writing and/or marking fluid according to claim 1, wherein said hard resin is a polyurethane polyol resin.

4. The writing and/or marking fluid according to claim 1, wherein at least one of formaldehyde releasers, phenoxyethanol, parabens or isothiazolinones is used as said preservative.

5. The writing and/or marking fluid according to claim 1, wherein said silicone wetting agent is a polyethylene-modified polysiloxane.

6. The writing and/or marking fluid according to claim 1, further comprising further wetting agents including glycerin and/or glycols or polyalcohols.

7. The writing and/or marking fluid according to claim 6, wherein said further wetting agents are added in an amount up to 15 wt % of the total weight of the whitish writing and/or marking fluid.

8. The writing and/or marking fluid according to claim 1, further comprising additives selected from the group consisting of antiblocking additives, colloidal dispersion of silicon dioxide particles, and polyether-modified polydimethylsiloxanes.

9. The writing and/or marking fluid according to claim 8, wherein the additives are added in a total amount of up to 10 wt % of the total weight of the whitish writing and/or marking fluid.

10. The writing and/or marking fluid according to claim 1, further comprising blue dyes or pigments in a concentration of no more than 0.2 wt % of the total weight of the whitish writing and/or marking fluid.

11. The writing and/or marking fluid according to claim 1, further comprising dyes or pigments in a concentration of no more than 3.0 wt % in an amount up to 15 wt % of the total weight of the whitish writing and/or marking fluid.

12. The writing and/or marking fluid according to claim 1, wherein the whitish writing and/or marking fluid is a white writing and/or marking fluid for capillary writing instruments.

13. The writing and/or marking fluid according to claim 1, wherein said aqueous dispersion of titanium dioxide is 55 to 60 wt % of the total weight of the whitish writing and/or marking fluid.

14. A writing instrument, comprising:
   a writing tip made of a capillary material;
   a reservoir made of another capillary material; and
   a writing and/or marking fluid disposed in said reservoir, said writing and/or marking fluid having:
      a viscosity of less than 30 mPa s;
      an aqueous dispersion of titanium dioxide in an amount of 45 to 70 wt % of a total weight of the whitish writing and/or marking fluid, a solid content of said aqueous dispersion of titanium dioxide being 70 to 75 wt % of said aqueous dispersion;
      an anionic dispersion of a hard resin in an amount of 5 to 15 wt % of the total weight of the whitish writing and/or marking fluid;
      a silicone wetting agent in an amount of 1.0 to 3.0 wt % of the total weight of the whitish writing and/or marking fluid;
      a preservative; and
      a remainder of water.

15. The whitish writing and/or marking fluid according to claim 1, wherein said viscosity is less than 30 mPa s when measured at 20° C. with a Brookfield cone and plate viscometer using a cone spindle CPE-40.

16. The writing instrument according to claim 14, wherein said viscosity is less than 30 mPa s when measured at 20° C. with a Brookfield cone and plate viscometer using a cone spindle CPE-40.

* * * * *